United States Patent [19]

Cohen et al.

[11] Patent Number: 4,815,469
[45] Date of Patent: Mar. 28, 1989

[54] IMPLANTABLE BLOOD OXYGEN SENSOR AND METHOD OF USE

[75] Inventors: Donald M. Cohen, Encino; James E. Barcel, Simi Valley; Michael D. Hooven, Valencia, all of Calif.

[73] Assignee: Siemens-Pacesetter, Inc., Sylmar, Calif.

[21] Appl. No.: 166,580

[22] Filed: Mar. 10, 1988

Related U.S. Application Data

[63] Continuation-in-part of Ser. No. 107,062, Oct. 8, 1987, abandoned.

[51] Int. Cl.$^4$ .............................. A61B 5/00
[52] U.S. Cl. ........................ 128/634; 128/419 PG; 364/413.09
[58] Field of Search ............ 128/633, 419 PG, 634; 364/413, 417

[56] References Cited

U.S. PATENT DOCUMENTS

| | | | |
|---|---|---|---|
| 3,123,066 | 3/1964 | Brumley | 128/2 |
| 3,461,856 | 8/1969 | Polanyi | 128/2 |
| 3,911,905 | 10/1975 | Rossel | 128/697 |
| 4,202,339 | 5/1980 | Witzfeld et al. | 128/419 PG |
| 4,232,679 | 11/1980 | Schulman | 128/419 PG |
| 4,399,820 | 8/1983 | Witzfeld et al. | 128/633 |
| 4,727,879 | 3/1988 | Liess et al. | 128/633 |
| 4,750,495 | 6/1988 | Moore | 128/419 PG |

Primary Examiner—A. Michael Chambers
Attorney, Agent, or Firm—Bryant R. Gold; Leslie S. Miller

[57] ABSTRACT

An implantable medical sensor (42) determines the oxygen content of blood. The sensor includes a miniaturized hybrid circuit (130) that includes light-emitting diode means (32), phototransistor means (34, 36), and a substrate (110) to which the light-emitting diode means and phototransistor means are bonded in a desired circuit configuration. The hybrid circuit is hermetically sealed within a cylindrical body (140) made from a material that is substantially transparent to light, such as glass. Feedthrough terminals (132, 134) provide means for making an electrical connection with the hybrid circuit. The light-emitting diode means is driven with a stair-stepped current pulse. In one embodiment, the sensor is embedded within a bilumen pacemaker lead (60) and positioned near the distal electrode (66) of the lead so that the sensor resides within the heart when the lead is implanted within a patient, thereby allowing the sensed oxygen content ($MVO_2$ concentration) of the blood within the heart to be a physiological parameter that can be used to control the pacing interval of a rate-responsive pacemaker (56).

34 Claims, 8 Drawing Sheets

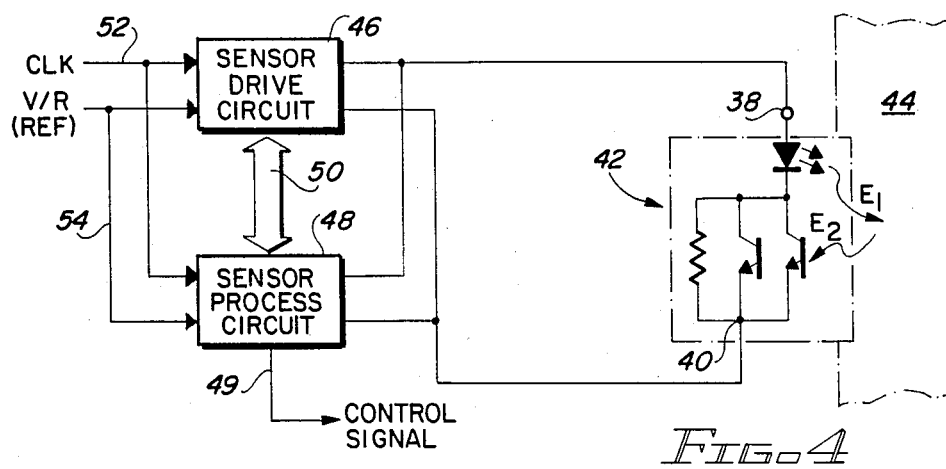
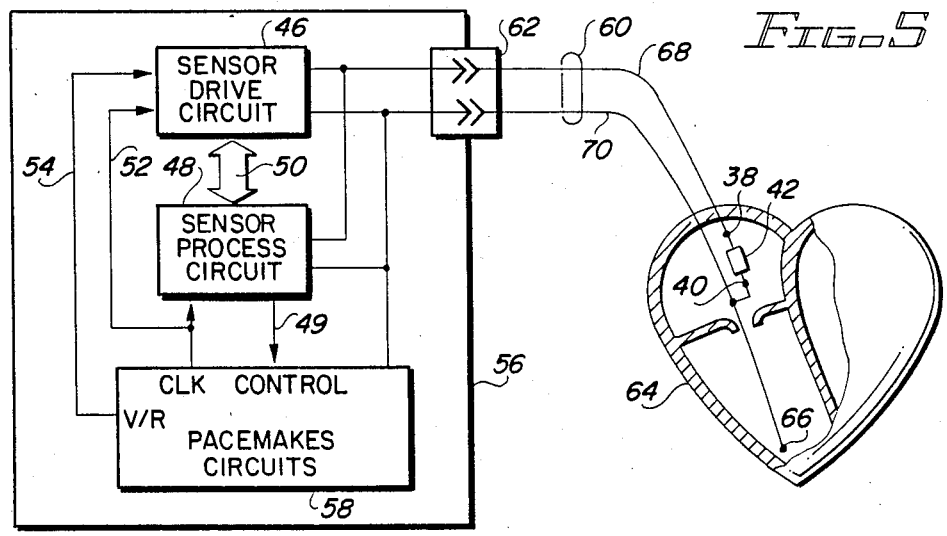
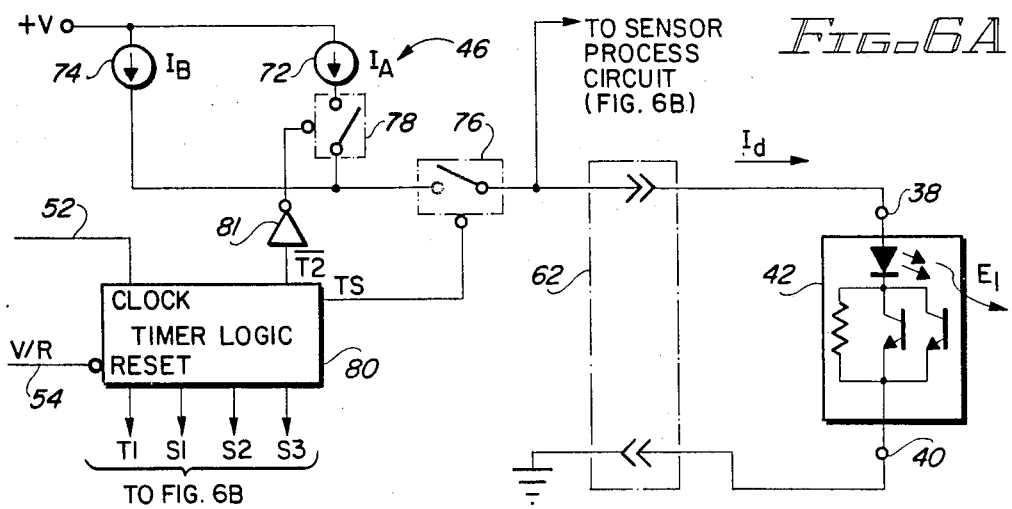

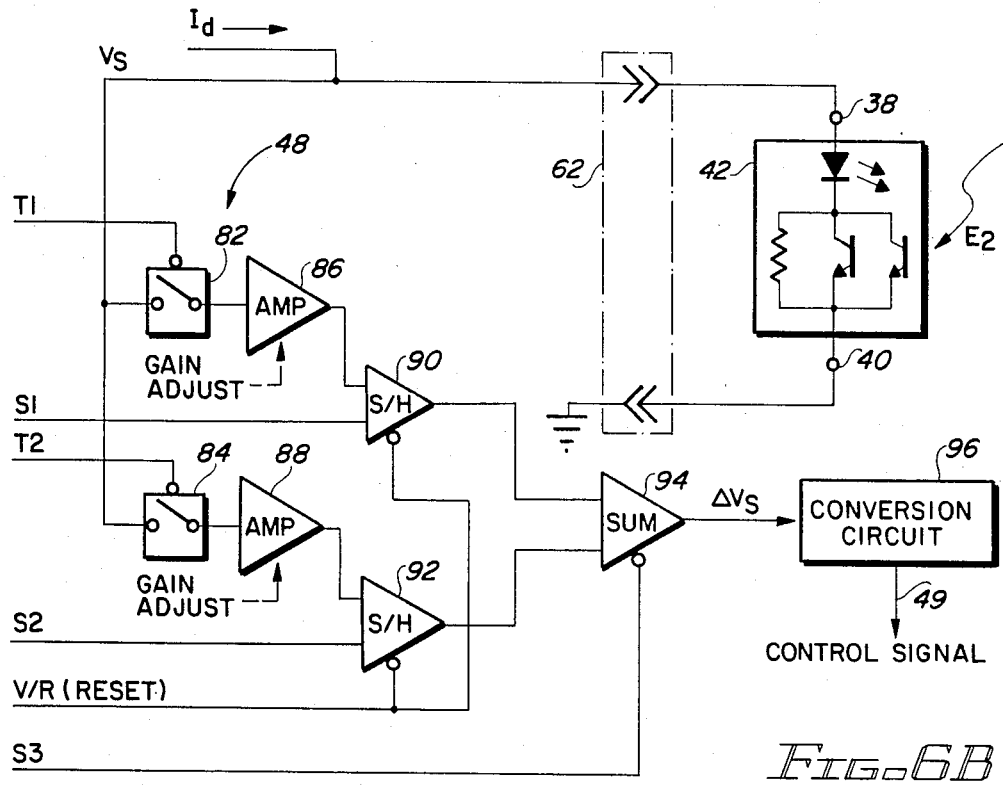
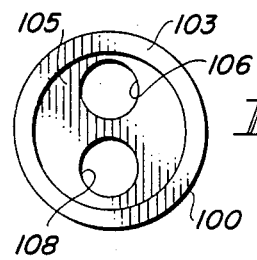
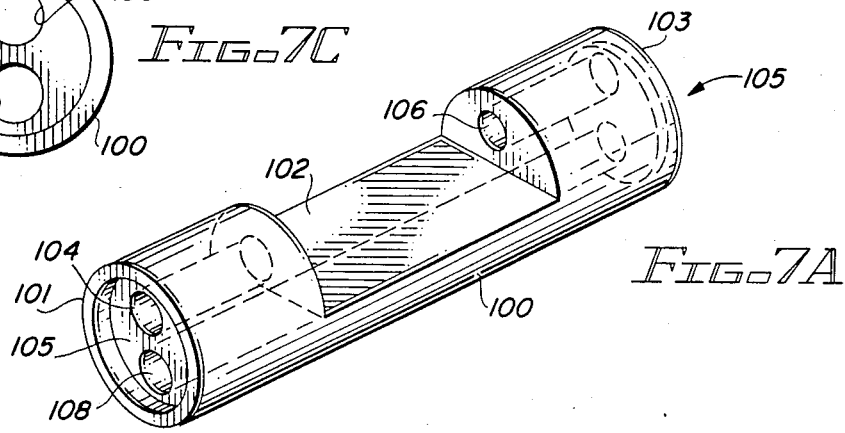
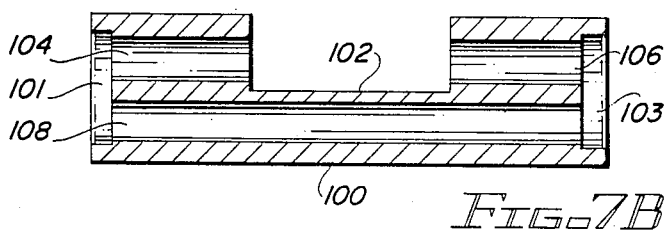

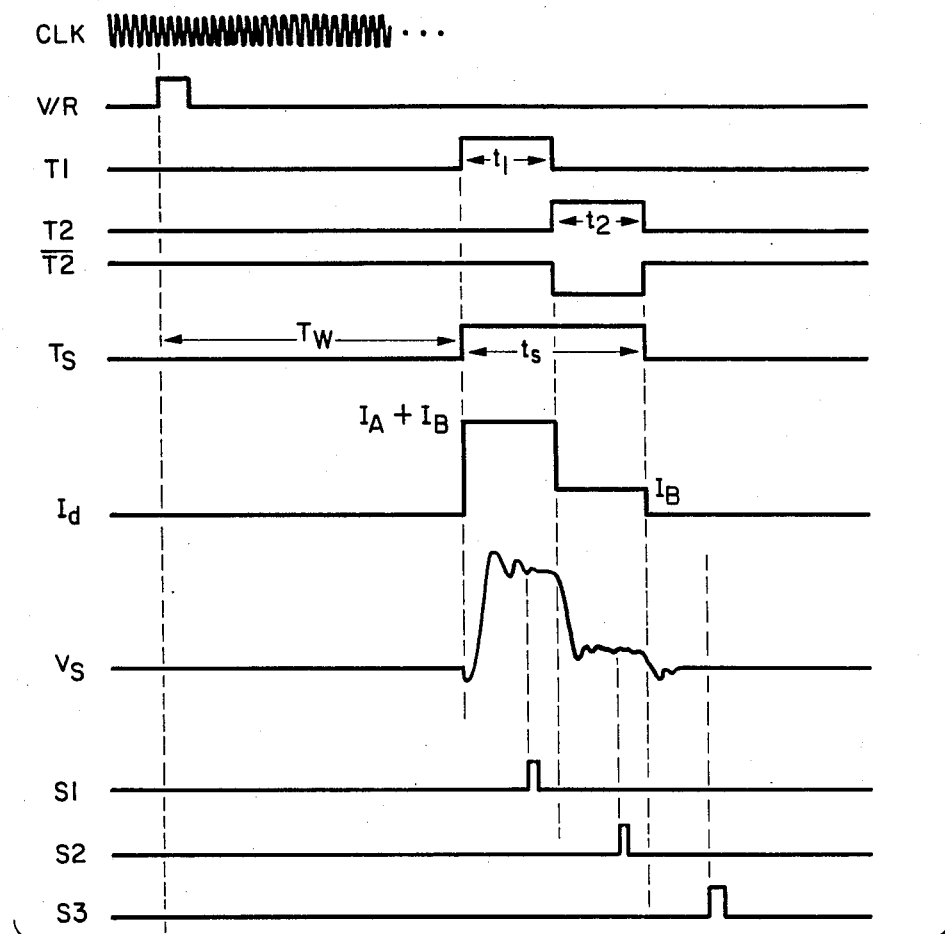
FIG.-6C
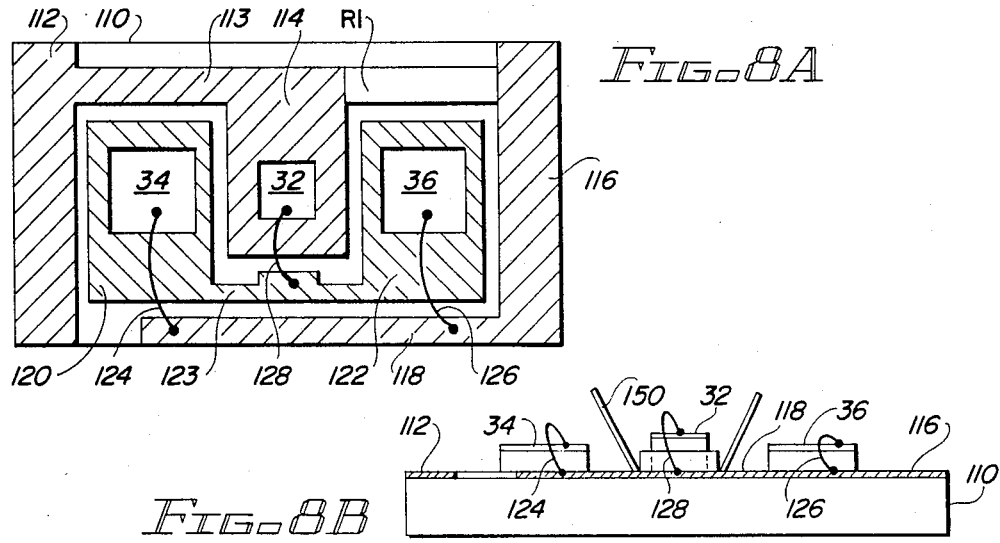
FIG.-8A
FIG.-8B

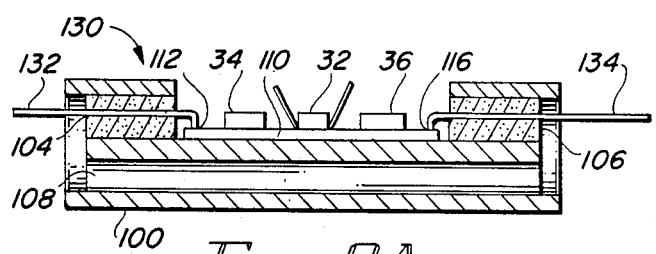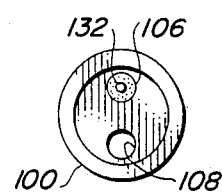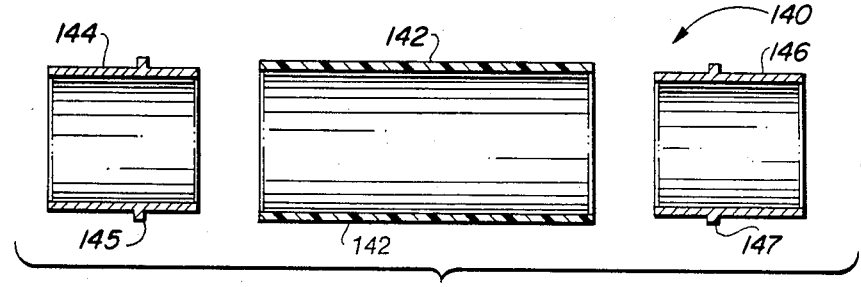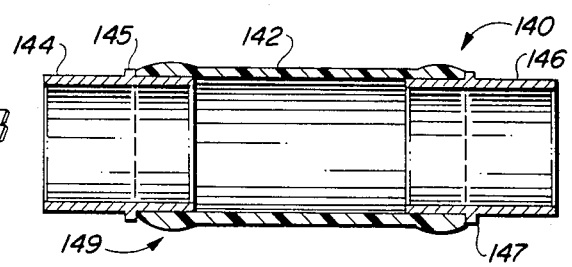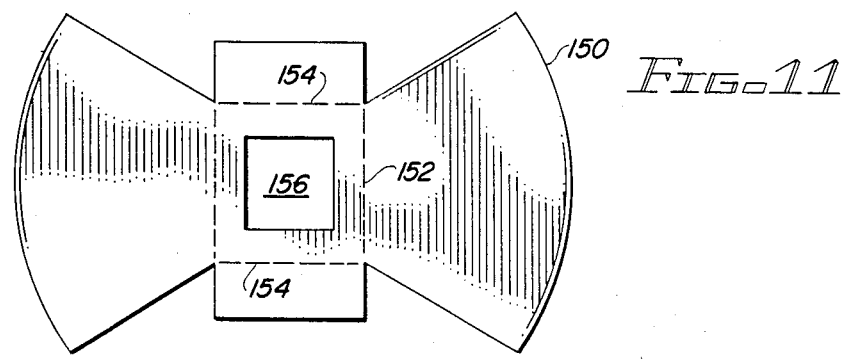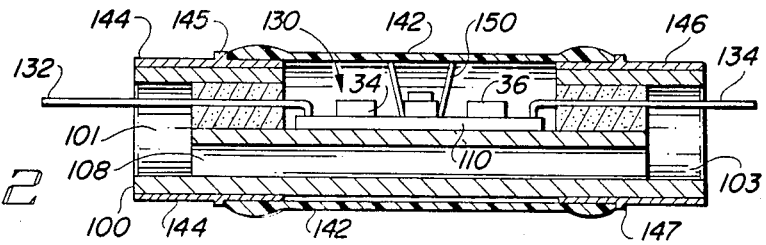

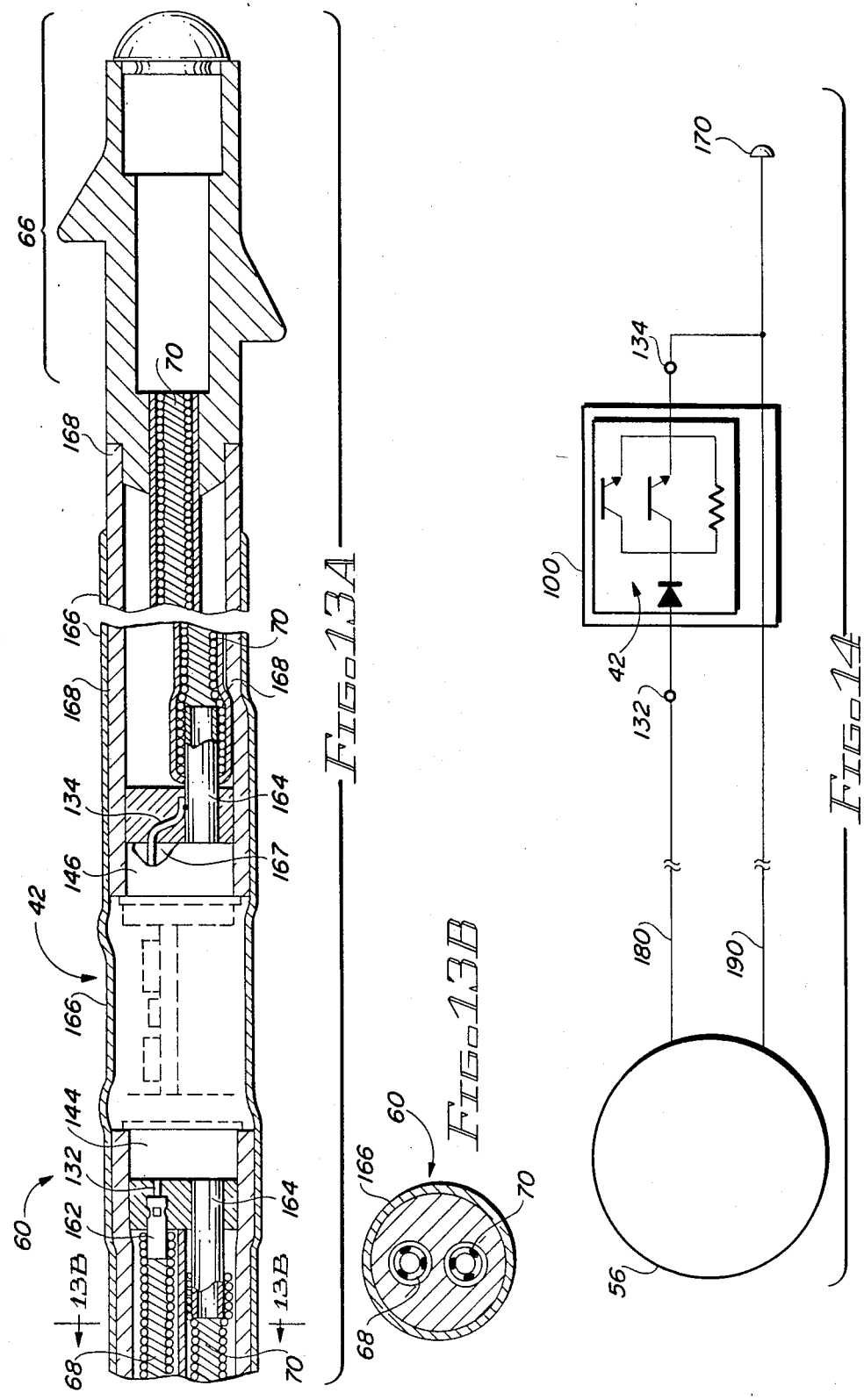

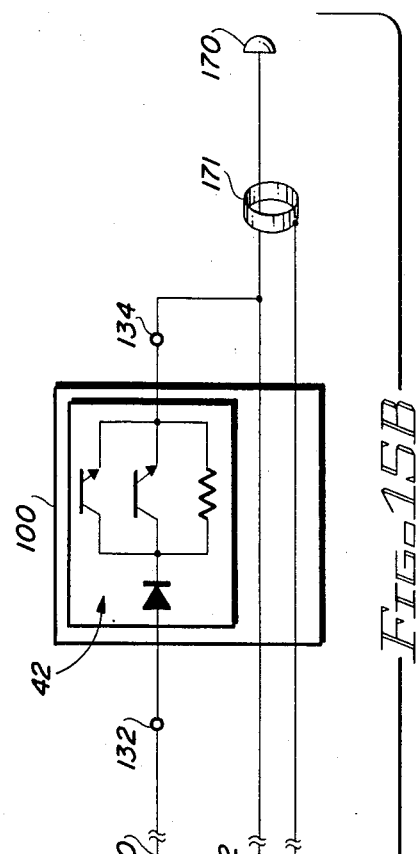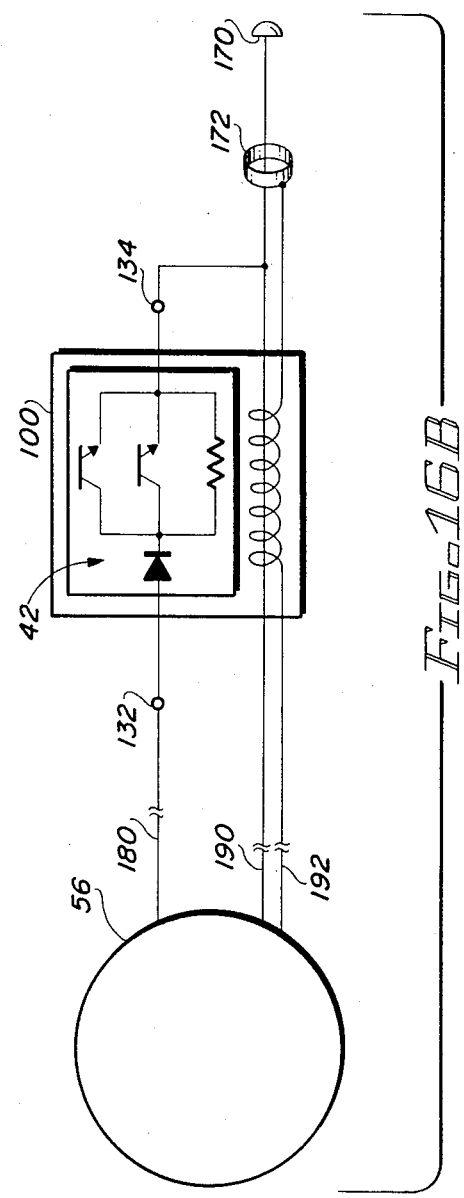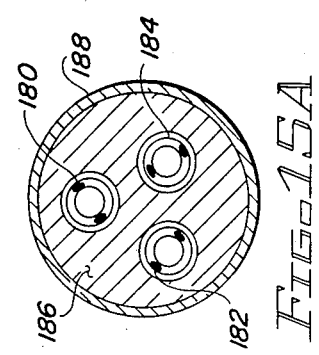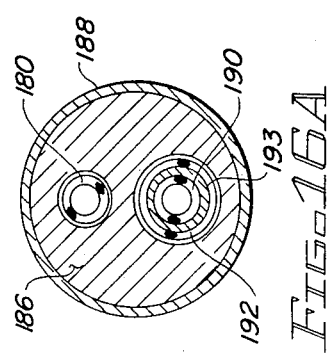

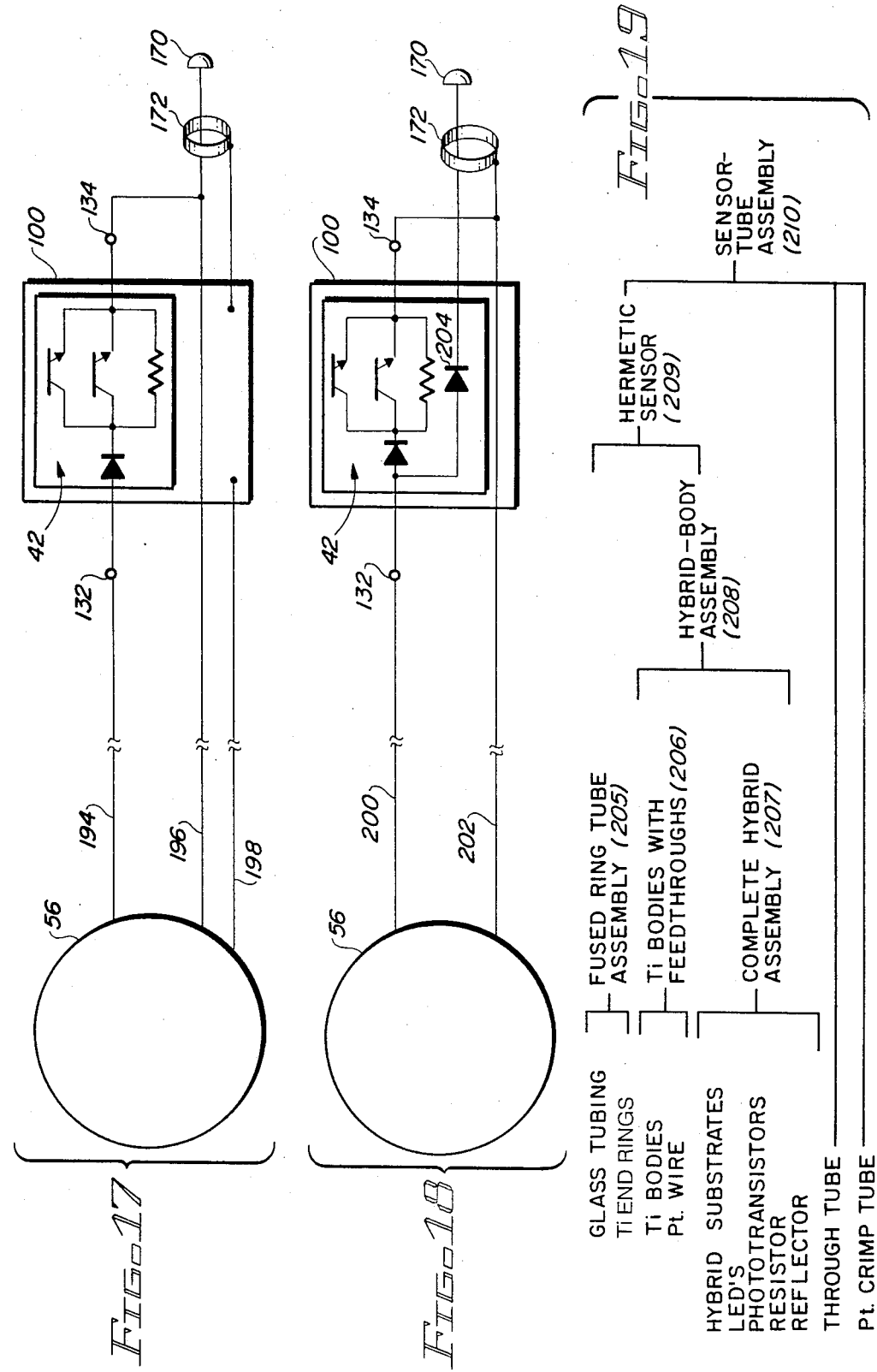

IMPLANTABLE BLOOD OXYGEN SENSOR AND METHOD OF USE

This application is a continuation-in-part of application Ser. No. 107,062, filed Oct. 8, 1987 now abandoned.

BACKGROUND OF THE INVENTION

The present invention relates to implantable medical devices, and more particularly to an implantable medical sensor that can be used to determine the oxygen content of blood. In a preferred embodiment, the sensor is housed in a miniature hermetically-sealed capsule that is embedded into an implantable pacemaker lead of a rate-responsive pacemaker.

It is known in the art to use an implantable sensor to determine the oxygen content of blood. It is also known in the art to utilize such a sensor in combination with a pacemaker in order to adjust the pacing interval or frequency of the pacemaker as a function of the oxygen content of the blood. See U.S. Pat. Nos. 4,202,339 and 4,399,820. Further, as described in U.S. Pat. No. 4,399,820 (hereafter the '820 Patent), the prior art recognizes the advantages of incorporating an oxygen sensor made from a light-emitting diode (LED) and a light receiving transistor, or phototransistor (PT), into an implantable cardiac pacing lead.

Unfortunately, the pacing system, including the lead and sensor, described in the '820 Patent, while representing a significant advance in the art at the time of its development, still exhibits some problems which have heretofore hindered a widespread clinical use of such a pacing system. For example, while the LED and PT elements used to realize the oxygen sensor of the pacing system taught in the '820 patent are advantageously embedded into the pacing lead, they are done so in a way that does not guarantee a true hermetic seal, there being at least one annular insulation layer 35 through which body fluids seep into the otherwise closed area where the LED element 32 and PT element 37 are located. Further, given the relatively large size of the annular elements used to create the pocket within which the LED and PT are located, e.g., the glass ring 39, and metal annular elements 31 or 31' and 34 or 34', the glass ring having a diameter approximately the same as the lead diameter, and given that the annular metallic elements have an outside diameter that must be firmly welded to the glass ring all around the circumference thereof, there is a relatively large weld that must not develop any leaks. This is not an easy task using conventional bonding techniques, especially given the periodic forces that are regularly placed on the lead as it moves or flexes within the heart or body.

Thus, disadvantageously the sensor taught in the '820 Patent is not easily sealed and protected from body fluids that might find their way into the lead, and even if it is initially sealed, it may not remain so with use. Needless to say, the presence of such body fluids within the lead could dramatically alter the optical properties and performance of the sensor system, as well as, the pacer output capabilities. Further, the arrangement shown in the '820 patent is very expensive, both in manufacturing time and cost. What is needed, therefore, is a more economical sealed sensor that can more readily be embedded into a pacing lead and that will remain tightly sealed throughout the life of the lead.

SUMMARY OF THE INVENTION

The present invention provides a miniaturized implantable medical sensor that optically senses the oxygen content of a body fluid to which the sensor is exposed, such as blood. In its completed form, the sensor is only about 0.3 inches long and 0.1 inches in diameter. Advantageously, the sensor includes an economical hybrid circuit, comprising a light-emitting diode (LED), at least one phototransistor, and one resistor, all mounted on a hybrid substrate which is in turn mounted on a titanium sensor body, the body and components all being inserted into a cylindrical sleeve. The sleeve is an assembly made of a length of glass tubing, comprised of soda lime glass with metal rings fused to each end. The ends of the cylindrical assembly are sealed to the titanium body through the use of titanium end rings. The titanium rings are permanently bonded to the walls of the glass tubing by applying heat at a specified temperature, which heat causes a permanent chemical bond to form between the titanium and the glass. Platinum feedthrough terminals pass through feedthrough holes in the sensor body and provide a means for making electrical contact with the hybrid circuit. These feedthrough holes are sealed with a high alumina (a type of ceramic) frit. The sealed sensor is embedded into a pacing lead and positioned near the distal end of such lead so that when the lead is implanted within a patient's heart, the sensor also resides in, or is near, the heart. Electrical contact is made with the sensor by connecting its feedthrough terminals to appropriate electrical conductors within the lead, which may be the conductors used for pacing/sensing of the heart.

In operation, the LED of the sensor is, in a preferred embodiment, energized with a stair-stepped current pulse. Energizing the LED with two known current levels in this fashion allows for meaningful analysis of the voltage-current relationship of the particular sensor used regardless of individual variations that exist between the components of the sensor, the lead conductors, or the ambient temperature.

When used with a pacemaker or similar stimulating device, the present invention thus provides a body-implantable sensor and lead that includes an implantable stimulating lead having a connector at one end thereof and electrode means at the other end thereof, the electrode means comprising means for electrically contacting body tissue when the lead is implanted in a body, and the connector comprising a means for interfacing the lead, both electrically and physically, with the desired stimulating device; a first insulated conductor having a distal end coupled to the electrode means and a proximal end coupled to the connector; sensor means forming an integral part of the lead for quantitatively sensing a specified characteristic of a body fluid proximal the sensor means, the sensor means including means responsive to a drive signal for generating an output signal that varies as a function of the specified body fluid characteristic; and means for transmitting the drive signal and the output signal between the sensor means and the connector.

The present invention also includes a method of using a medical sensor that has light-emitting diode means for emitting a light pulse that is directed to a desired type of organic material to be analyzed, which light pulse is then received by phototransistor means, a desired property of the organic material being determinable in accordance with the manner in which at least one detectable property of the light pulse is affected by the organic material; the method comprising the steps of: (a) exciting the light-emitting diode means with a first drive current for a first period of time; (b) exciting the light-emitting diode means with a second drive current for a second period of time immediately subsequent the first period of time; (c) monitoring the light pulses received by the phototransistor means during the first and second periods of time to determine the change in the light pulses as a result of having come in contact with the organic material; and (d) processing the amount of change identified in step (c) to determine a desired property of the organic material.

BRIEF DESCRIPTION OF THE DRAWINGS

The above and other advantages and features of the present invention will be more apparent from the following more particular description thereof, presented in conjunction with the following drawings, wherein:

FIG. 4 is block diagram illustrating the manner in which the oxygen sensor of FIG. 2 is used to sense the reflective properties of blood, which reflective properties vary as a function of the oxygen content of the blood;

FIG. 5 is a block diagram showing the sensor of FIG. 2 inserted into the pacing lead of a rate-responsive pacing system;

FIG. 6A is a functional schematic diagram of a circuit configuration that is used to realize the sensor drive circuit of FIG. 4;

FIG. 6B is a functional schematic diagram of a circuit configuration that is used to realize the sensor process circuit of FIG. 4;

FIG. 6C is a timing diagram showing the inter-relationship between various key signals used by the system of FIG. 5 and the circuits of FIGS. 6A and 6B;

FIG. 7A is a perspective view of a preferred sensor body;

FIG. 7B is a sectional view of the sensor body of FIG. 7A;

FIG. 7C is an end view of the sensor body of FIG. 7A;

FIG. 8A is a top view of a hybrid version of the sensor circuit of FIG. 2 realized on a ceramic substrate (for clarity, reflector 150 is omitted form this view);

FIG. 8B is a side view of the hybrid circuit of FIG. 8A;

FIG. 9A is a side view of a sensor body assembly, and shows the hybrid circuit of FIG. 8 mounted to the sensor body of FIG. 7, and shows feedthrough pins passing through the sensor body for the purpose of making electrical contact with the hybrid circuit;

FIG. 9B is an end view of the sensor body assembly of FIG. 9A;

FIG. 10A is an exploded side section view of a sensor lens assembly;

FIG. 10B is a side view of the assembled lens assembly of FIG. 10A;

FIG. 11 is a view of a reflector element before forming that may be inserted around the LED of the hybrid circuit;

FIG. 12 is a side view of the complete sensor assembly, including body, hybrid circuit, feedthroughs, lens, and reflector;

FIG. 13A is a side view of the sensor assembly of FIG. 12 embedded into a bilumen pacing lead;

FIG. 13B is a cross-sectional view of the lead of FIG. 13A taken along the lines 13B—13B;

FIG. 14 is a schematic representation of the lead of FIG. 13A;

FIG. 15A is a cross-sectional view of one embodiment of a bipolar pacing lead wherein the sensor assembly of FIG. 12 is embedded;

FIG. 15B is a schematic representation of the lead of FIG. 15A;

FIG. 16A is a cross-sectional view of another embodiment of a bipolar pacing lead wherein the sensor assembly of FIG. 12 is embedded;

FIG. 16B is a schematic representation of the lead of FIG. 16A;

FIG. 17 is a simplified schematic representation of a pacemaker and a bipolar pacing lead into which the sensor assembly of the present invention is embedded;

FIG. 18 is an alternative embodiment of a pacemaker and a bipolar pacing lead into which the sensor assembly of the present invention is embedded; and FIG. 19 illustrates a process assembly tree for the sensor assembly.

DETAILED DESCRIPTION OF THE INVENTION

Figure 1:
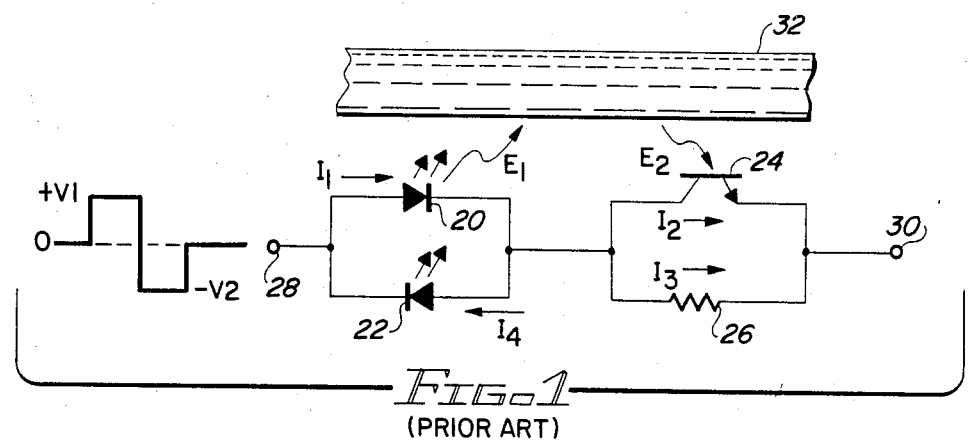
FIG. 1 is a schematic diagram of an oxygen sensor of the prior art.

The following description is of the best presently contemplated mode of practicing the invention. This description is not to be taken in a limiting sense but is made merely for the purpose of describing the general principles of the invention. The scope of the invention should be ascertained with reference to the appended claims.

The invention will be described with reference to the drawings, wherein like numerals (or equivalent reference designators) are used to designate like parts throughout the following description. In order to better understand the present invention, it will help to first understand the operation of an oxygen sensor of the type that is known in the art. Accordingly, reference is first made to FIG. 1 wherein the schematic diagram of an oxygen sensor of the prior art is illustrated. The sensor includes two light-emitting diodes 20 and 22 connected in parallel, with the anode of diode 20 being connected to the cathode of diode 22, and the anode of diode 22 being connected to the cathode of diode 20. A phototransistor 24 is connected in parallel with a resistor 26, and the collector of the phototransistor 24 is connected to the same node as is the anode of diode 22 and the cathode of diode 20. The node comprising the anode of diode 20 and the cathode of diode 22 comprises one input terminal 28, and the emitter of phototransistor 24 and one side of the resistor 26 comprises another terminal of the sensor 30.

In operation, a bi-phase voltage pulse is applied across terminals 28 and 30. This bi-phase voltage pulse is also illustrated in FIG. 1 and includes a positive portion, having an amplitude of $+V1$; followed by a negative portion, having a negative amplitude of $-V2$. The positive portion of the bi-phase voltage pulse causes a current $I_1$ to flow through light-emitting diode 20, thereby causing light energy $E_1$ to be emitted by the LED 20. The light $E_1$ comes in contact with a desired body fluid 32, such as blood. Depending upon the properties of the fluid 32, a portion of the light energy $E_1$ is reflected back to the phototransistor 24. In FIG. 1, as well as in the other figures, that portion of light energy reflected back to the phototransistor is identified as $E_2$. Thus, in FIG. 1, the amount of current $I_2$ that flows through phototransistor 24 is a function of the light energy $E_2$ that is incident upon the base of the phototransistor 24. The balance of the current $I_1$ that does not flow through phototransistor 24, therefore, flows through the resistor 26. This current is identified as $I_3$. Thus, it is seen that $I_1$ is equal to $I_2$ plus $I_3$. The current $I_2$ varies as a function of the light energy $E_2$, thereby also affecting the amount of current $I_3$ that flows through resistor 26. The voltage developed across terminals 28 and 30 (which voltage is a function of the forward drop across LEd 20 and the voltage drop across resistor 26 caused by the current flow $I_3$) will thus vary as a function of the reflected light energy $E_2$ that is incident upon the phototransistor 24. Hence, by monitoring the voltage across the terminals 28 and 30, it is possible to get an indication of the reflectance properties of the fluid 32.

In order to determine the amount of voltage variation across terminals 28 and 30 caused by the current $I_2$, it is necessary to isolate other variations in this voltage from the measurement. This is typically done by causing current $I_4$ to flow through resistor 26 and LED 22 during the negative portion of the bi-phase voltage waveform. During this portion of the wave form, both the phototransistor 24 and LED 20 are back biased, and therefore no current flows through either of these devices. The value of $I_4$ is selected to be close to the value of $I_1$ so that the forward voltage drop across LED 20 will be approximately the same as the forward voltage drop across LED 22. As can be appreciated by those skilled in the art, this technique works only if LED 20 and LED 22 are closely matched. Further, the method assumes that negligible leakage currents flow through phototransistor 24 and LED 20 when such are back biased. The technique is further complicated by the fact that a bi-phase voltage wave form must be generated, which typically requires more than one voltage source, or a complicated biasing scheme. Further, the configuration of FIG. 1 employs just one phototransistor 24 to receive the reflected light energy $E_2$. The sensitivity of the circuit to changes in the reflected properties of the fluid 32 would be vastly improved if additional phototransistors could be employed. Unfortunately, in order to keep the physical size of such sensors very small, such devices cannot use more than about four elements as shown in FIG. 1: two LED's, one phototransistor, and one resistor.

Figure 2:
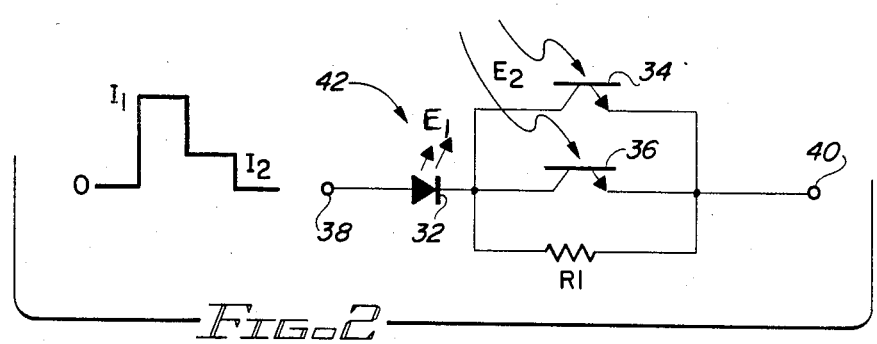
FIG. 2 is a schematic diagram of an oxygen sensor in accordance with the present invention.

In order to overcome these problems, the present invention provides a sensor 42 as shown in FIG. 2. Sensor 42 includes a single LED 32 connected in series with a parallel network made up of a first phototransistor 34, a second phototransistor 36, and a resistor R1. Advantageously, the configuration shown in FIG. 2, like that of FIG. 1, is limited to four elements, and therefore the size can be made very small. Further, the configuration of FIG. 2 uses only one LED 32, which LED 32 need not be matched with any other LED. A significant advantage of the circuit of FIG. 2 is that two phototransistors are employed rather than one. Each phototransistor is capable of receiving the reflected light energy, $E_2$, thereby significantly improving the sensitivity of the device. Another advantage of the circuit configuration of FIG. 2 is that only one voltage source is required, the LED 32 being driven by a stair-stepped current pulse. A first portion of the current pulse provides a drive current $I_1$ that causes LED 32 to emit light energy $E_1$. The second portion of the stair-stepped current pulse provides a current $I_2$, which is chosen to effectively be on the knee of the voltage-current characteristic transfer curve of the LED 32. That is, the current $I_2$, is selected at a low value at which very little, if any, light energy $E_1$ is emitted by the diode $E_2$.

At either current level, the voltage developed and measured thus provides an indication of impedance at that current level. Hence, a differential measurement may be made between the voltage for (or other parameter) developed at current value $I_1$ and at current value $I_2$, which differential measurement can be used in a variety of ways, such as is discussed in connection with FIG. 3.

Figure 3:
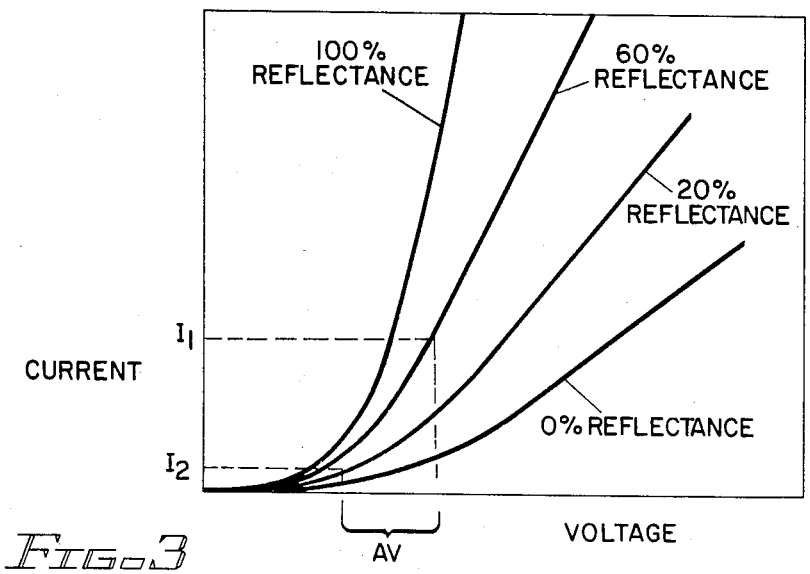
FIG. 3 is a representtive family of curves showing the voltage-current relationship of the sensor of FIG. 2.

FIG. 3 depicts a family of curves showing the voltage-current relationship of the sensor of FIG. 2. The change in voltage developed across terminals 38 and 40 of sensor 42 of FIG. 2 provides an accurate measurement of the amount of reflected light energy received by photo-transistors 34 and 36. Hence, by monitoring this change in voltage, the sensor 42 of FIG. 2 is able to provide an indication as to the reflective properties of the fluid 32 to which the light energy $E_1$ is exposed. These reflective properties, in turn, can be correlated to a desired property of the fluid 32, such as the oxygen content of the fluid. This correlation is known and documented in the art.

Referring next to FIG. 4, a block diagram is shown illustrating the manner in which the oxygen sensor 42 of FIG. 2 is used to sense the reflective properties of blood. The sensor of FIG. 2, identified in FIG. 4 as the sensor 42, is positioned within an area of a living body where blood 44 is able to come in contact with the light energy $E_1$ emitted by the sensor. Typically, the sensor 42 will be placed within a vein that is carrying blood back to the lungs, or within the heart itself. A sensor drive circuit 46 provides the stair-stepped current pulse needed to drive the sensor 42. Similarly, a sensor process circuit 48 monitors the voltage developed across the sensor terminals 38 and 40. Approximate timing signals 50 are shared between the sensor drive circuit 46 and the sensor process circuit 48. Further, in order to synchronize the sensing function of the sensor 42 with other events, the sensor drive circuit 46 and the sensor process circuit 48 typically receive a clock signal 52 and a timing reference signal 54 from a location external to these circuits. For example, when the sensor 42 is used with an implanted cardiac pacemaker, the clock signal 52 is obtained from the circuits within the pacemaker. Similarly, the reference signal 54 is typically a signal indicating a cardiac event, such as a V-pulse or R-wave signal, which signals indicate that the ventricle of the heart has either been paced or that a ventricular contraction has been sensed.

The use of the sensor 42 with an implanted rate-responsive pacemaker 56 is further illustrated in FIG. 5. In FIG. 5, it is seen that the drive circuit 46 and the sensor circuit 48 are included within a pacemaker housing, which housing is made to be implantable in a human body. Included within the rate-responsive pacemaker 56 are conventional pacemaker circuits 58. The drive circuit 46 and the sensor circuit 48 are coupled to the pacemaker circuits 58 in the manner above-described. That is, the clock signal 52, as well as a V/R signal (signifying either an R-wave has been sensed or a V-stimulation pulse has been generated) are provided from the pacemaker circuits 58 to the drive circuit 46 and the sensor circuit 48. A pacing lead 60, connected to the pacemaker housing 56 by way of a conventional bipolar pacer connector 62, allows the pacemaker to deliver stimulation pulses to a heart 64 at a distal electrode tip 66 through conductor 70. This same conductor 70 allows the pacemaker circuits to sense cardiac events occurring ner the lead tip 66. The sensor 42 is advantageously embedded within the pacemaker lead 60 at a location near the distal tip so as to place the sensor 42 within the heart 64. Further, when positioned properly within the heart, the lead is curved in a manner that causes the sensor to face blood just prior to the blood's passage through the heart's tricuspid valve. The terminal 38 of the sensor 42 is connected to a separate conductor 68 of the lead 60. The other terminal 40 of the sensor 42 is connected within the lead to the conductor 70. The sensor process circuit 48 develops a control signal 49 that is representative of the reflectance properties of the blood (and hence relatable to the amount of oxygen that has been sensed within the blood). This control signal 49 is presented to the pacemaker circuits 58 and is used as a physiological parameter to control the rate at which the pacemaker circuits deliver a stimulation pulse to the heart. Thus, the configuration shown in FIG. 5 is representative of a rate-responsive pacemaker wherein the rate of the pacemaker varies as a function of the sensed oxygen content of the blood that comes in contact with the sensor 42.

Referring next to FIGS. 6A, 6B, and 6C, functional schematic diagrams of the sensor drive circuit 46 (FIG. 6A) and the sensor process circuit 48 (FIG. 6B) are shown. Also included, in FIG. 6C, is a timing diagram showing the interrelationship between various key signals used by the circuits of FIGS. 6A and 6B. In FIG. 6A, it is seen that the sensor drive circuit 46 comprises a first current source 72 (that provides a first current $I_A$) and a second current source 74 (that provides a second current $I_B$). The current source 74 is connected to the terminal 38 of the sensor 42 by means of a first switch 76. The current source 72 is switchably connected in parallel with the current source 74 by means of another switch 78. The switches 76 and 78 are controlled by logic signals generated by timer logic 80. As depicted in FIG. 6A, a high logic signal applied to the control input of switches 76 and 78 causes the switches to close. The timer logic 80 generates appropriate timing signals T1, T2, TS, S1, S2 and S3, having a relationship as shown in FIG. 6C. A clock signal 52, and a reset signal 54 (which may be the V/R signal from the pacemaker) are also provided as input signals to the timer logic 80. Conventional circuitry within timer logic 80, known to those skilled in the art, is used to generate the signal patterns shown in FIG. 6C.

As depicted in FIG. 6C, the V/R signal 54 resets the timer logic 80. As previously indicated, the V/R signal indicates that the ventricle of the heart has been paced with a V stimulation pulse, or that an R-wave has been sensed, indicating a natural contraction of the ventricle. In either event, there is a certain time period after such event during which the heart is refractory and the pacemaker circuits are inoperative. It is during this time period that the sensor 42 can be pulsed in order to measure the oxygen content of the blood. Thus, at a desired time $T_W$ after the V/R signal, a sample pulse $T_S$ is generated. This sample pulse $T_S$ may be further divided into a first portion $t_1$ and a second portion $t_2$. During the sample pulse $T_S$, the switch 76 is closed, thereby allowing the current $I_B$ from current source 74 to flow through the sensor 42. Further, during all but the time period $T_2$, the switch 78 is closed, thereby allowing the current $I_A$ from current source 72 to also flow to the sensor 42 when switch 76 is closed. The net effect of this action is to have both currents $I_A$ plus $I_B$ flow through the sensor 42 during time $t_1$, and having only current $I_B$ flow through the sensor 42 during time $t_2$. Thus, the desired stair-step current pulse is provided to the sensor 42. Typically, the energizing of the sensor 42 will occur some 10–20 milliseconds after the V/R signal (that is, $T_W$ is approximately 10–20 milliseconds), however, it is to be understood that other times could be used. The width of $t_1$ and $t_2$ is on the order of 120 microseconds, thereby providing a total sensor measurement time of 240 microseconds. The stair-stepped current provided to the sensor 42 is represented in FIG. 6 as the drive current $I_d$. Typically, $I_B$ has a value of about 0.3 ma, and $I_A$ has a value of about 0.9 ma (making the maximum drive current equal to about 2.0 ma).

Referring next to FIG. 6B, the functional schematic diagram of the sensor process circuit 48 is depicted. It is the function of this circuit to measure the voltage developed across the sensor 42 during each portion $t_1$ and $t_2$ of the time $T_S$ during which the sensor 42 is active. This is accomplished through the use of two sample pulses S1 and S2. As seen in FIG. 6C, the sample pulse S1 occurs during the latter portion of the time $t_1$ of signal T1, and the sample pulse S2 occurs during the latter portion of the time $t_2$ of the signal T2. The sampling is done towards the latter portion of each of these sample times in order to allow the voltage developed across the sensor 42, $V_S$, to settle down before the measurement is made.

Referring again to FIG. 6B, it is seen that the sensor processor circuit 48 connects the terminal 38 of the sensor 42 to amplifiers 86 and 88 through switches 82 and 84 respectively. Switch 82 is closed during time T1, and switch 84 is closed during time T2. The outputs of amplifiers 86 and 88 are fed into the inputs of sample and hold circuits 90 and 92, respectively. Sample signal S1 controls the operation of the sample and hold circuit 90; while the sample signal S2 controls the operation of the sample and hold circuit 92. Both sample and hold circuits 90 and 92, as well as the amplifiers 86 and 88, and the switches 82 and 84 (and the switches 76 and 78) are of conventional design. It is the function of the sample and hold circuits 90 and 92 to present and hold at the output terminal the voltage appearing at the input terminal during the sample time.

The output of the sample and hold circuits 90 and 92 is directed to a conventional differential amplifier or summing circuit 94. During sample time S3, which is subsequent the energization of the sensor 42 by a few milliseconds, the differential amplifier 94 has as inputs two voltages held by the respective sample and hold circuits 90 and 92 in order to determine the difference therebetween. This difference in voltage corresponds to the difference in voltage represented in the family of curves of FIG. 3, and is therefore relatable to a particular reflectance value. Hence, the conversion circuit 96, uses this difference voltage in order to generate the control signal 49 that provides a quantitative measure of the reflectance properties measured. Advantageously, this control signal can be presented to the rate-responsive pacemaker circuits in order to control the pacing interval thereof, as shown in FIG. 5.

In a preferred embodiment, the rate-responsive pacemaker circuits 58 (FIG. 5) include a microprocessor. Hence, the conversion circuit 96 is implemented using appropriate analog-to-digital conversion techniques and a subroutine within the microprocessor that converts the digitized difference voltage presented thereto to a particular reflectance amount. In turn, this reflectance amount is converted to an appropriate control voltage that is used to adjust the pacing interval of the pacemaker circuits, using conventional rate-responsive pacemaker control techniques.

It is noted, with reference to FIG. 6B, that the gain of amplifiers 86 and 88 can be selected as desired in order to optimize the performance of the sensor processor circuit 48. The gain of each amplifier is preferably a programmable parameter that can be adjusted, using conventional programming techniques, in order to achieve a desired result. Reference is made to U.S. Pat. No. 4,232,679 for teaching the fundamentals of programming various parameters in order to alter the operation or performance of an implanted device, including changing the gain of an amplifier.

Referring next to FIGS. 7A, 7B, and 7C, there is shown a perspective, sectional view and end view, respectively, of a sensor body 100. As indicated in FIG. 7A, the sensor body 100 comprises a cylindrical shaped member, a center portion of which has been removed so as to provide a flat portion 102 upon which the sensor circuitry, as described below, may be mounted. Circumferential ridges 101, 103 at each end of the body 100 define recessed end portions 105. These ridges advantageously provide a uniform thickness welding surface to which titanium rings 144 and 146 can be welded, as described below. A hole 104 passes through one end of the sensor body 100 to the platform area 102; similarly, another hole 106 passes through the other end of the sensor body 100 to the platform area 102. A larger hole 108, passes through the entire length of the sensor body 100 under the platform area 102.

In the preferred embodiment, the sensor body is made from titanium. It has a length of approximately 0.3 inches, and a diameter of approximately 0.1 inches.

The sensor circuitry is mounted on a ceramic substrate 110, as shown in FIGS. 8A and 8B. FIG. 8A shows a top view of the ceramic substrate and FIG. 8B shows a side view thereof. The ceramic substrate 110 has conductive regions (a metallic layer) deposited and etched thereon using conventional techniques. As shown in FIG. 8A, there are three conductive areas or regions (distinguished by a different style of cross-hatching), each electrically insulated from the others, that are placed on the substrate 110. A first conductive region connects one end 112 of the substrate with a center area 114 by way of a conductive track 113. A second conductive region connects the other end of the substrate 116 to a front edge of the substrate 118. Finally, a third conductive region connects a first pad area 120 with a second pad area 122 by means of a conductive track 123. The anode of LED 32 (see FIG. 2) is bonded to the central pad or conductive area 114 using a conductive polymer, in conventional manner. (A conductive reflector 150, shown in FIGS. 11 and 12 may be first bonded to area 114, with the cathode of LED 32 being bonded to the reflector 150. However, for clarity, this reflector 150 is omitted from FIG. 8A.) Similarly, the collector of phototransistor 34 is bonded to pad 120, and the collector of phototransistor 36 is bonded to pad 122. This bonding is done using a commercially available bonding methods, such as eutectic bonding techniques. A thin film resistor of an appropriate value is deposited or otherwise placed on the ceramic substrate 110 in conventional manner so as to be electrically connected between pad area 114 and the end portion of the substrate 116. In the preferred embodiment, this resistor R1 has a value of approximately 500 ohms. A first bonding wire 124 is connected between the emitter of phototransistor 34 and the front edge conductive area 118. Similarly, another bonding wire 126 connects the emitter of phototransistor 36 and the area 118. Finally, still another bonding wire 128 connects the cathode of LED 32 to the conductive track 123 that connects the pad 120 to the pad 122. Conventional hybrid circuit mounting and bonding techniques are used in order to bond the LED and phototransistors to their desired locations on the ceramic substrate 110, and in order to connect the bonding wires 124, 126 and 128 to their desired locations.

Referring back to FIG. 7, the short holes 104 and 106 of the sensor body 100 provide a means for allowing feedthrough wires 132 and 134 (FIG. 9) to pass from the sensor end 105 to the flat center portion 102. Feedthrough wires 132 and 134 are, in the preferred embodiment, made from 0.005 inch diameter 80/20 platinum-irridium (Pt-Ir) wire. It has been shown in the prior art that the Pt-Ir material is very stable, with a tendency to neither migrate nor oxidize. The contact that the Pt-Ir makes with the printed gold on the circuit is quite reliable. A high $Al_2O_3$ frit is preformed over respective lengths of such wire, and the wire-coated-with-frit is inserted into holes 104 and 106. The sensor body and frit are then fired at a temperature and duration compatible to form a hermetic, biocompatible, stable seal in holes 104 and 106 through which the feedthrough wires 132 and 134 pass.

After the sensor body 100 has the feedthrough wires 132 and 134 inserted and sealed into holes 104 and 106, it is combined with the hybrid assembly of FIG. 8 to form a sensor body assembly 130 as shown in FIGS. 9A and 9B. The bottom side of the ceramic substrate 110 is bonded to the platform area 102 of the sensor body. The feedthrough wires 132 and 134 are then bent and welded to the end pads 112 and 116, respectively, of the ceramic substrate 110. The pins 132 and 134 thus provide a means for making electrical contact with the sensor circuitry located on the substrate 110. It is noted that the pin or feedthrough 132 electrically corresponds to the terminal 38 in FIG. 2, and the pin or feedthrough 134 electrically corresponds to the terminal 40 in FIG. 2.

With reference now to FIG. 10A, an exploded side sectional view of a sensor lens assembly 140 is shown. This assembly includes a glass tube 142 to which two end rings 144 and 146 will be attached. FIG. 10B shows the sensor lens assembly 140 in its assembled form. The end rings 144 and 146 are slideably inserted into desired locations at each end of the glass tube 142 until ridges 145 (on the outer diameter of end ring 144) and ridge 147 (on the outer diameter of end ring 146) abut up against the end of the glass tube 142. Heat is then applied to each end of the glass tube 142 in order to permanently bond the end rings 144 and 146 to the glass tube. This heat is applied by inductive heating of the metal rings 144 and 146. A temperature of around 700 degrees centigrade for 30–60 seconds is used for this purpose. Applying this amount of heat causes the glass tube to deform slightly as shown at 149 in FIG. 10B.

In the preferred embodiment, the glass tube 142 is soda lime glass. This type of material advantageously chemically reacts with the titanium end rings 144 and 146 when heat is applied as above described in order to form a very tight, chemical bond between the titanium end rings and the glass tube.

For the seal to be made reliably, several conditons must be satisfied. The temperature coefficients of expansion and contraction of the two materials must be matched to within a few parts per million per degree Celcius. The wall thicknesses, particularly of the metal rings, must be small (in the case of the metal rings, 0.002 inches). The annular clearance between the glass and metal must be uniform and small. The temperature to which the glass is heated must exceed the softening point without reaching the melting point. This temperature must be controlled such that there are not more than trivial, tensile residual stresses in the glass upon recovery to normal dimensions near room temperature.

Referring next to FIG. 11, there is shown a view of an unformed reflector 150 that is designed to be inserted around and/or under the LED 32 on the ceramic assembly 130. The reflector is machined by standard photo chemical etching means. The reflector may, in a subsequent operation, be formed into the appropriate shape by a tool and die. Large wings of the reflector 150 are folded along lines 152, and the short stubs of the reflector 150 are folded along the lines 154. The folded reflector assembly is, in the preferred embodiment, placed under the LED 32 during assembly. The reflector is made of a conductive material, such as brass or titanium. Once in place, the reflector will electrically connect the LED 32 to pad 114. Attachment is made with conductive adhesive, such as Ag epoxy or Polyimide. The reflector serves two purposes: (1) it increases the light launched into the blood that would otherwise not directly impinge upon the lense; and (2) it reduces the amount of light traveling directly from the LED to the phototransistor without first interacting with the blood.

Next, referring to FIG. 12, a sectional view of the completed sensor assembly 42 is shown. This assembly includes the sensor lens assembly 140 into which the hybrid sensor assembly 130 has been inserted. The titanium sensor body 100 is laser welded to the titanium end rings 144 and 146 using conventional laser welding techniques. The ends of the sensor body have been designed to simplify the laser welding process and to decrease the rejection ratio of this procedure. Flanges 101, 103 provide ends that form uniform, thin surfaces for welding to the metal rings of the lense assembly. The annular clearance between the rings and the body is kept to less than a few thousandths of an inch. This requires strict adherence to tolerances on the linearity of the lense assembly. The weld flanges offer the following advantages. They permit low laser energy to be used for the welding process since both metal pieces are thin. They allow a strong weld, since both the rings and the flanges are of similar thickness. They allow a uniform laser power density to be used since the flanges are of a constant wall thickness. Furthermore, they increase the separation between the high intensity laser beam and the susceptible components, e.g., feedthrough glass and electronics.

Once this weld has been completed, the hybrid sensor assembly 130 is totally sealed within the sensor assembly. Typically, the tightness or hermeticity of the seal is tested to at least $10^{-8}$ cc air/sec at one atmosphere pressure. However, even though thus sealed, the sensor circuit can readily function as above-described in connection with FIGS. 2-6 by applying the appropriate drive signals or voltage measurement signals to the feedthrough pins 132 and 134. Advantageously, light emitted by the LED 32 is directed by the reflector 150 up through the soda lime glass sensor wall 142. Any reflections of this light can then similarly pass back through the lens 142 to the phototransistors 34 and 36. The sensor is shown in FIG. 12 can thus be incorporated within a desired measurement system and implanted within a patient for the purpose of sensing the reflective properties of a body fluid to which the sensor is exposed.

In the preferred embodiment, the sensor utilizes spectrophotometric analysis of the reflectance of light by blood (a body fluid). This principle has been described in the art, and it has been shown that reflectance is related to oxygen saturation. That is, oxygen saturation of whole blood can be estimated by analyzing the optical intensity of reflected light. For purposes of the present application, this means that the degree of light reflectance incident on the phototransistors 34 and 36 at a wavelength of 660 nm is a function of the mixed venous oxygen ($MVO_2$) concentration in the blood. A high $MVO_2$ concentration will reflect more light to the phototransistors, while a lower $MVO_2$ concentration will reflect less. It has been determined that roughly 18% reflectance occurs for the highest possible concentration of $MVO_2$ in the blood. This reflectance value varies to 0% as the $MVO_2$ concentration changes. (It is noted that in FIG. 3, the curve labeled 100% corresponds to the maximum reflectivity possible.) Furthermore, sensor signal amplitude is directly proportional to the intensity of the reflected light.

As has been indicated, in the preferred embodiment, the sensor 42 is embedded within a pacing lead 60 as shown in FIG. 13A. The pacing lead 60 is preferably a bilumen pacing lead having two conductors 68 and 70 passing through most of the length thereof. These conductors may be of conventional type, typically realized with a helically wound conductive wire. A cross-sectional view of the bilumen portion of the pacing lead 60 is shown in FIG. 13B It is noted that while a bilumen pacing lead is shown in FIGS. 13A and 13B, a coaxial type pacing lead could also be employed for the lead, and conventional breakout techniques could be used to separate the two coaxial conductors so that they could interface with the sensor as shown in FIG. 13A. In practice, such conventional break-out techniques are used towards the proximal end of the lead 60, not shown in FIG. 13A, in order to allow a conventional coaxial bipolar connector to interface with the pacemaker connector 62.

In FIG. 13A, the feedthrough pin 132 is connected to the conductor 68 using a conventional crimp connector 162. The materials selected for the crimp connector 162 and the conductor 68 should not create a galvanic potential that would promote corrosion. In the preferred embodiment, Pt-Ir and stainless steel provide a strong, non-corrosive bond. A stylet tube 164, made from stainless steel hypodermic tubing, coated with a thin polyimide coating over the portion of the tubing that may come in contact with the titanium sensor body 100, is passed through the lower hole 108 of the sensor. (Polyimide is a commercially available insulation material.) The purpose of the polyimide coating is to insulate the stylet tube 164 from the titanium sensor body 100. (Such insulation is optional, but is believed to be beneficial in order to prevent the sensor body 100 from acting as an electrode when a high current stimulation pulse passes through the lead conductor 70.) The helically wound conductor 70 is connected to the stylet tube 164 in a conventional manner at both ends of the stylet tube. In the preferred embodiment, the stylet tube 164 is of the same material as the helically wound conductor 70. The feedthrough terminal 134 is bent down to make contact with the stylet tube 164 and is welded or bonded to the stylet tube using conventional laser welding or other bonding techniques. Epoxy fills the space between the protruding portions of the end rings 144 and 146, and further helps to seal the entire assembly.

Advantageously, a thin layer of polyurethane 166, or other suitable material, coats the length of the lead 60 along the length of the lead where the sensor is located. (This thin layer 166 could also coat much of the length of the lead, as is commonly done with many pacing leads.) This coating is in addition to the silicone rubber tubing 168 that forms the outer body of the lead. The polyurethane layer 166 is substantially transparent to the light energy emitted by the LED 32 (which light has a wavelength on the order of 660 nm). Advantageously, the polyurethane coating presents a transparent medium for light transmission and a benign coating which minimizes tissue growth, thereby keeping the "window" through which the light energy must pass, relatively clean.

The manner of making and assembling a pacemaker lead of the type shown in FIG. 13 is known in the art. What primarily distinguishes the lead 60 from conventional pacing leads is the use of the sensor 42, and the manner in which conductor 70 passes through the sensor body 100.

A schematic representation of the pacemaker lead of FIG. 13A is shown in FIG. 14 wherein a pacer 56 has a two-conductor lead attached thereto. A first conductor 180 attaches to the input terminal 132 of the sensor 42. A second conductor 190 passes through the sensor and is attached to a tip electrode 170, and to the output terminal 134 of sensor 42.

As an additional embodiment, it should be noted that the sensor 42 could also be incorporated into a bipolar pacing lead. If bipolar pacing is employed, two conductors need to pass by the sensor in order to make electrical contact with the tip and ring electrodes of the bipolar lead, respectively. If a separate additional conductor is used to contact the sensor, the body of the bipolar lead (assuming the sensor 42 is embedded near the distal tip of the lead) must have three conductors therein. One possible configuration to achieve this result is a trilumen lead of the type shown in the sectional view of FIG. 15A and the schematic representation of FIG. 15B, wherein a first conductor 180, a second conductor 182, and a third conductor 184 are encased in silicone rubber 186, which is coated with a thin layer of polyurethane 188. Thus, for the tri-lumen embodiment of FIG. 15, the titanium sensor body 100 (FIG. 7) has two long holes 108 passing through the lower half thereof.

Another possible configuration is a bilumen pacing lead as shown in the sectional view of FIG. 16A and corresponding schematic representation of FIG. 16B. FIGS. 16A and 16B are similar to FIGS. 15A and 15B, respectively, but the lower lumen of FIG. 16A contains coaxial conductors 190 and 192, with conductor 190 being of a smaller diameter helix and inside of the larger helix of conductor 192, each insulated from the other with conventional insulating material 193. In FIG. 16B, it is seen that the innermost conductor 190 of the coaxial conductors goes to the tip electrode 170 and to the sensor output 134. The outer conductor 192 goes to the ring electrode 172 of the bipolar lead.

It should also be pointed out that the titanium sensor body 100 is itself an electrical conductor. As such, the body itself, or a contiguous portion of it could function as the ring electrode in a bipolar mode. Alternatively, one of the conductive paths through the sensor assembly (to reach a distal tip or ring electrode, or to make contact with the return pin 134 of the sensor 42) could be the titanium body 100. In accordance with this approach, a conductor within the lead is securely attached to the proximal end of the sensor body 100, and a continuation of this conductor is attached to the distal end of the sensor body 100. This approach is schematically illustrated in FIG. 17, wherein a pacemaker 56 has a three-conductor lead attached thereto. A first conductor 194 attaches to the input terminal 132 of the sensor 42. A second conductor 196 passes through the sensor and is attached to a tip electrode 170, as well as the output terminal 134 of the sensor 42. (The attachment of the terminal 134 could be made internal to the sensor 42, if desired.) A third conductor 198 is electrically attached to the proximal end of the titanium body 100. The ring electrode 172 is attached to the distal end of the titanium body 100.

Advantageously, the configuration of FIG. 17 can be used to pace in either a unipolar or bipolar mode of operation. During unipolar operation, no signals or voltage potentials are applied within the pacer 56 to conductors 194 or 198. Rather, a negative pacing pulse is applied to conductor 196, and the positive voltage potential within the pacemaker 56 is applied to the can or case of the pacemaker 56 in conventional manner. Thus, the distal tip 170 paces unipolarly, cathodically. During operation of the sensor 42, the desired sensor drive signal is applied to conductor 194, and the negative voltage potential within the pacemaker 56 is applied to conductor 196. The can of the pacemaker 56 is allowed to float (not connected to any voltage potentials). Thus, current passes only through the sensor, not through the tip electrode 170.

During a bipolar pacing operation, no signals or voltage potentials are applied to conductor 194. A negative pacing pulse is applied to conductor 196 and the positive voltage within the pacemaker 56 is connected to conductor 198, which positive voltage is electrically connected to ring electrode 172 by way of the conductive titanium sensor body 100. This negative voltage also appears at the output terminal 134 of the sensor 42, but because the sensor 42 is floating (no signals connected to input terminal 132), this voltage does no harm. During operation of the sensor 42, the sensor drive signal is applied to conductor 194, and the negative voltage potential within the pacemaker 56 is applied to conductor 196. The can or case of the pacemaker 56 floats. Thus, current passes only through the sensor, not through the tip electrode 170.

Referring to FIG. 18, there is shown still another embodiment of the present invention used with a bipolar pacing lead configuration in which the pacing lead contains only two conductors 200 and 202. A blocking diode 204 is added to the sensor circuit. In accordance with this approach, both conductors of the lead are used during sensor operation: conductor 200 for the drive signal connected to the input terminal 132 of sensor 42 and conductor 202 for the return path connected to the output terminal 134 of sensor 42. Similarly, both conductors are used during conventional bipolar pacing/sensing: conductor 200 being connected to the tip electrode 170 through diode 204 and conductor 202 being connected to the ring electrode 172. During operation of the sensor 42, the sensor drive signal is applied to conductor 200, and the negative voltage is applied to conductor 202, which back biases the diode such that current passes only through the sensor, not through the tip electrode 170. Thus, both conductors within the lead are used for two functions. This embodiment assumes that the sensor 42 is not operational at a time when the tip/ring electrodes of the pacing lead are operating. Fortunately, as has been explained previously in connection with FIGS. 5–6, a pacemaker is not operative during a refractory time period, and the sensor 42 could thus operate during this refractory time period.

As with the configuration of FIG. 17, the configuration of FIG. 18 can be used advantageously to pace in either a unipolar or a bipolar mode of operation. Unipolar pacing is achieved by floating conductor 202, applying a negative pacing pulse to conductor 200, and connecting the positive voltage potential of the pacemaker to the case or can of the pacemaker 56. Bipolar pacing is achieved by applying a negative pacing pulse to conductor 200, floating the pacemaker case, and connecting the positive voltage potential to conductor 202. Sensor operation is achieved by connecting the sensor drive signal to conductor 200, connecting the negative voltage potential of the pacemaker 56 to conductor 202, and floating the pacemaker case. These connections for each of these operations of the configuration shown in FIG. 18 are summarized in Table 1.

TABLE 1

| Conductor | Bipolar Pacing | Unipolar Pacing | O$_2$ Sensing |
|---|---|---|---|
| 200 | − | − | + |
| 202 | + | Float | − |
| Case/Can | Float | + | Float |

Representative switching circuitry needed within the pacemaker 56 in order to effectuate the various connections summarized in Table 1 may be carried out as detailed, for example, in pending patent application PACEMAKER HAVING PROGRAMMABLE CONFIGURATION, Ser. No. 896,542, filed Aug. 13, 1986, assigned to same assignee as is this application (the '542 application). The '542 application is incorporated herein by reference.

It is noted that the operation described above in configuration with FIG. 18 assumes an ideal blocking diode 204. In practice, there will be a voltage drop across diode 204 in the forward direction and a leakage current will flow in the reverse direction. However, by properly choosing the characteristics of the diode 204, any adverse impact caused by these "real-life" parameters can be minimized or eliminated.

It is further noted that the blocking diode 204 could be eliminated, thereby simplifying the number of components involved. However, if diode 204 is removed, the sensing drive signal could potentially stimulate the heart. This should not happen, however, if the sensing drive signal is synchronized with the heart's refractory period, as it would be as described above. This is because the heart is not capable of being stimulated while it is refractory.

FIG. 19 provides a sensor process development tree of the assembly procedure. The main processes are described below.

The Fused Ring-Tube Assembly 205 includes fusing the glass tube and the two titanium end seal rings, wherein the seal produced must be hermetic, fitting well over the titanium sensor body and removing any oxides therefrom. Platinum-irridium feedthroughs and the titanium sensor body are fired to produce Titanium Bodies with Feedthroughs 206 wherein said feedthroughs must be hermetic, insulated, and able to withstand laser weld. The Complete Hybrid Assembly 207 comprises the hybrid substrate, one LED, two phototrasistors, one resistors, and the reflector. The assembled hybrid must pass conventional hybrid lab quality control (Q.C.) requirements, laser weld, long-term aging, and shock under load. The Hybrid-Body Assembly 208 is formed by bonding the hybrid substrate to the titanium sensor body and welding the feedthroughs to the hybrid substrate. The mounted Hybrid-Body Assembly 208 must then pass laser weld, thermal aging, and shock. To provide a hermetic seal over the sensor, the Hybrid-Body Assembly 208 is slideably mounted into the Fused Ring-Tube Assembly 205 and laser welded to produce the Hermetic Sensor 209 such that the titanium-glass tube forms a hermetic seal with the titanium body with only minimal residual stress on the glass and no effect on the hybrid. Finally the proximal platinum-irridium feedthrough is crimped to proximal portion of the conductor. The other feedthrough is welded to the stylet tube on the distal side. Epoxy is potted between the protruding protions of the end rings. The resultant Sensor-Tube Assembly 210 must provide a reliable connection to the lead coils and insulation and pass a high potential (Hypot) dielectric test.

The LED 32 of the sensor 42, in the preferred embodiment, is a commercially available LED chip, type URDA-35E, commercially available from Shin-Itzu. The phototransistors 34 and 36 are likewise commercially available components, type F50B, available from Siemens. Equivalent devices are available from numerous other manufacturers. As has been indicated, oxygen staturation of the blood is estimated by analyzing the optical intensity of reflected light at a specific wavelength (660 nm).

As thus described, a hermetically sealed sensor is disclosed that can advantageously be embedded within a pacing lead adapted for implantation within a human body. In order to sense the reflective properties of the blood to which the sensor is exposed, and in order to avoid interference with the normal operation of the pacemaker, the sensor can be activated during a time when the pacing lead is not being used by the pacemaker. These sensed reflective properties, in turn, provide an indication of the oxygen content of the blood. This information is then processed and used by a rate-responsive pacemaker in order to adjust the pacing interval of the pacemaker in an appropriate manner.

While the invention described herein has been described with reference to a particular embodiment and application thereof, numerous variations and modifications could be made thereto by those skilled in the art without departing from the spirit and scope of the invention as claimed. For example, while the sensor has been described as being placed in one chamber of the heart, it could also be placed (for some purpose) in the other chamber of the heart, or in another location where it would be exposed to the fluid being monitored. Similarly, many variations are possible relative to how the sensor is mounted in a pacing lead, what type of pacing lead is used, if any, and low electrical contact is made with the sensor. Accordingly, the true scope of the invention should be determined with reference to the claims set forth below.

What is claimed is:

1. A body-implantable sensor and lead comprising:
an implantable stimulating lead having a connector at one end thereof and electrode means at the other end thereof, the electrode means comprising means for electrically contacting body tissue when the lead is implanted in a body, and the connector comprising a means for interfacing the lead, both electrically and physically, with a desired stimulating device;
a first insulated conductor having a distal end coupled to the electrode means and a proximal end coupled to the connector;
sensor means forming an integral part of the lead for quantitatively sensing a specified characteristic of a body fluid proximal the sensor means, the sensor means including means responsive to a drive signal for generating an output signal that varies as a function of the specified body fluid characteristic;
means for transmitting the drive signal and the output signal between the sensor means and the connector; and
means for hermetically sealing said sensor means.

2. The body-implantable sensor and lead of claim 1 wherein said sensor means comprises
means for emitting a measuring signal into said body fluid in response to said drive signal; and
means for receiving a portion of said measuring signal reflected back to said sensor by the body fluid, the portion of the measuring signal reflected back to said sensor being proportional to the specified characteristic of said body fluid.

3. The body-implantable sensor and lead of claim 2 wherein said emitting means comprises means for emitting an optical signal, and said receiving means comprises means for receiving that portion of said optical signal that is reflected back into said sensor by the body fluid.

4. The body-implantable sensor and lead of claim 3 wherein said optical signal emitting means comprises a light-emitting diode (LED), and wherein said optical signal receiving means comprises at least one photo-sensitive semiconductor device, said LED and said photosensitive device being sealed within a housing that is embedded within said lead.

5. The body-implantable sensor and lead of claim 4 wherein said drive signal comprises a stair-step current pulse that excites said LED with a first current for a first time period and that excites said LED with a second current for a second time period immediately subsequent said first time period.

6. The body-implantable sensor and lead of claim 4 wherein said LED emits an optical signal having characteristics that cause the amount of the optical signal reflected back to the sensor to vary as a function of the oxygen content of the body fluid.

7. The body-implantable sensor and lead of claim 4 wherein said photo-sensitive semiconductor device comprises at least two phototransistors, each of which is mounted on a substrate; said LED also being mounted on said substrate; said substrate further having resistor means placed thereon for providing a specified resistance; said substrate having connection means thereon for connecting said phototransistors and said resistance means in a parallel network, and for connecting said LED in series with said parallel network; said substrate and the components mounted thereon being hermetically sealed in said housing, said housing having window means for allowing optical signals emitted by said LED, and optical signals received by said pair of phototransistors, to pass out of and into said sealed housing; said sealed housing further having feedthrough means for making electrical contact with the connection means on said substrate; said sealed housing being embedded within said lead.

8. The body implantable sensor and lead of claim 7 wherein said hermetically sealed housing comprises a hollow tube made from soda lime glass; said housing further comprises a titanium metal ring that is inserted into each end of said hollow tube; said metal ring having said feedthrough means sealably passing therethrough; said metal rings being sealably bonded to said hollow tube around the edges of said tube so as to form a tight seal of at least $10^{-8}$ cc air/sec at one atmosphere pressure, and wherein the sealed bonded between said metal rings and the edges of the hollow soda lime glass tube is a chemical bond formed between the titanium and the soda lime glass.

9. The body-implantable sensor and lead of claim 7 further comprising a diode and a second conductor; wherein said proximal end of said first conductor is coupled to said distal end of said first conductor through said diode; said proximal end is also electrically connected to said means for transmitting said drive signal to said sensor; said second conductor is electrically connected to a ring electrode located near a distal end of said second conductor and to said feedthrough means to said housing.

10. The body-implantable sensor and lead of claim 7 wherein said means for transmitting said drive signal to said sensor means comprises a second conductor coupled at a proximal end to said connector and coupled at a distal end to the feedthrough means of said housing.

11. The body-implantable sensor and lead of claim 10 wherein the feedthrough means of said housing is further coupled to said first conductor.

12. The body-implantable sensor and lead of claim 10 wherein said lead further includes a third conductor, electrically insulated from said first and second conductors, said third conductor being electrically connected to a ring electrode located near a distal end of said lead.

13. The body-implantable sensor and lead of claim 12 wherein said third conductor passes through a portion of said sensor means without making electrical contact therewith.

14. The body-implantable sensor and lead of claim 12 wherein said third conductor makes electrical contact with said sensor means.

15. The body-implantable sensor and lead of claim 12 wherein said first and third conductors are coaxial within said lead.

16. The body-implantable sensor and lead of claim 10 wherein said lead comprises a bipolar lead having a ring electrode and a tip electrode, and wherein said feedthrough means of said housing includes first and second feedthrough terminals, and further wherein one of said first and second conductors is electrically connected to said first feedthrough terminal, and the other of said first and second conductors is electrically connected to said second feedthrough terminal.

17. The body-implantable sensor and lead of claim 16 wherein said first and second conductors are coaxial within said lead.

18. The body-implantable sensor and lead of claim 10 wherein said lead further includes a third conductor, electrically insulated from said first and second conductors, said third conductor being connected to the proximal end of said housing, and wherein the body of said housing is also used as the ring electrode.

19. An implantable oxygen sensor and lead used with an implantable rate-responsive pacing system; said pacing system including timing means for generating timing signals and for defining a pacing interval, and pulse generator means for generating stimulating pulses at appropriate times within said pacing interval; said timing means including control circuits for automatically adjusting the pacing interval of said pacing system as a function of the oxygen content of body blood sensed by said oxygen sensor, said implantable oxygen sensor and lead comprising:
  means responsive to a drive signal for emitting a measuring signal into said body blood, said measuring signal being of a type that is affected by the oxygen content of said blood;
  means for receiving the measuring signal after it has been emitted into said body blood and affected by the oxygen content thereof;
  lead means for delivering the stimulation pulses from the pulse generator to a desired body location; an implantable hermetically sealed case within said lead means wherein said emitting means and receiving means are housed;
  control means for generating said drive signal; and
  processing means coupled to said receiving means for processing the receiving measuring signal and for generating an output signal indicative of the oxygen content of said blood.

20. The implantable oxygen sensor and lead of claim 19 wherein said control means and processing means are located within the rate-responsive pacemaker, and further including means for sensing signals between the control means and processing means within said pacemaker and the emitting means and receiving means within the hermetically sealed case of said sensor.

21. The implantable oxygen sensor and lead of claim 20 wherein the output signal of said processing means is coupled to the control circuits of said timing means, said output signal providing the basis for said control circuits to adjust the pacing interval of said pacemaker as a function of the sensed oxygen content of the blood.

22. The implantable oxygen sensor and lead of claim 21 wherein said emitting means comprises an LED that emits an optical signal having characteristics that cause the optical signal to be reflected back to the sensor as a function of the oxygen content of the blood, and further wherein said receiving means comprises at least two phototransistors, each of which is mounted on a substrate; said LED also being mounted on said substrate; said substrate further having resistor means placed thereon for providing a specified resistance; said substrate including connection means for connecting said phototransistors and said resistance means in a parallel network, and for connecting said LED in series with said parallel network; said substrate and the components mounted thereon being hermetically sealed in said case; said case having window means for allowing optical signals emitted by said LED, and optical signals received by said pair of phototransistors, to pass out of and into said case; said case having feedthrough means for making electrical contact with said substrate.

23. A hermetically sealed, implantable medical sensor used to sense a desired parameter associated with body tissue, including body fluids, in which said medical sensor is implanted, said sensor comprising:
  a hollow tube having sealed window means therein;
  a substrate inserted into said tube;
  light-emitting diode means placed on said substrate for emitting light of a prescribed frequency range in response to a drive signal, said light-emitting diode means being positioned on said substrate so as to permit at least a portion of said light to pass through said window means, contact body tissue outside of said window means, and reflect back through said window means;
  phototransistor means placed on said substrate for receiving light of a prescribed frequency range received through said window means, and for generating an output signal having characteristics that vary as a function of at least one parameter of the light received through said window means;
  connection means for connecting said light-emitting diode means and said phototransistor means is a desired circuit configuration, and for connecting a first terminal to said light-emitting diode means, and for connecting a second terminal to said phototransistor means;
  sealing means sealably secured to each end of said tube for sealing said substrate, light-emitting diode means, phototransistor means, and connection means within said tube, said sealing means including feedthrough means for making electrical contact from a point external said tube with said first and second terminals;
  means for generating said drive signal and applying it through said first and second terminals to said light-emitting diode means; and
  means for monitoring through said first and second terminals the output signal generated by said phototransistor means, and for processing said signal to provide a sensor signal indicative of said at least one parameter of the light received through said window means, said sensor signal thereby providing a measure of a desired characteristic of said body tissue as measured by the manner in which said at least one parameter of light is affected by coming in contact with said body tissue.

24. The medical sensor of claim 23 wherein said drive signal generating means includes means for generating a stair-stepped drive current tht excites said light-emitting diode means with a first current level for a first prescribed time period, and that excites said light-emitting diode means with a second current level for a second time period immediately subsequent to said first time period.

25. The medical sensor of claim 24 wherein said means for monitoring and processing the output signal generated by said phototransistor means comprises means for determining the amount of change in the output signal as a result of the change in the amount of light reflected back into said window means for said first time period to said second time period.

26. The medical sensor of claim 23 wherein said hollow tube is made from a material that is substantially transparent to the light emitted by said light-emitting diode means and the light received by said phototransistor means, said light transparent material thereby comprising the sealed window means through which said light passes.

27. The medical sensor of claim 26 wherein said hollow tube material comprises soda lime glass.

28. The medical sensor of claim 26 wherein said sealing means comprises a metal ring that is inserted into each each of said hollow tube, said metal ring having said feedthrough means sealably passing therethrough, said metal rings being sealably bonded to said hollow tube around the edges of said tube so as to form a tight seal of at least $10^{-8}$ cc air/sec at one atmosphere pressure.

29. The medical sensor of claim 28 wherein said metal rings are made from titanium, said hollow tube is made from soda lime glass, and wherein the sealed bond between said metal rings and the edges of the hollow soda lime glass tube is a chemical bond formed between the titanium and the soda lime glass.

30. The medical sensor of claim 23 wherein said light-emitting diode means comprises a light-emitting diode chip bonded to said substrate substantially in the center thereof, and further including a reflector envelope placed between said light-emitting diode chip and a portion of the window means of said hollow tube, whereby the light emitted by said light-emitting diode chip is directed substantially upward and out through said window means.

31. The medical sensor of claim 30 wherein said phototransistor means comprises at least two phototransistor chips that are bonded to said substrate, one phototransistor chip being positioned on one side of said light-emitting diode chip and reflector envelope, but still under a portion of said window means; and the other phototransistor chip being positioned on the other side of said light-emitting diode chip and reflector envelope, but still under another portion of said window means; said at least two phototransistor chips being electrically connected in parallel by said connection means.

32. A method of using a medical sensor that includes light-emitting diode means for emitting a light pulse that is directed to a desired type of organic material to be analyzed, which light pulse is then received by phototransistor means, a desired property of said organic material being determinable in accordance with the manner in which at least one detectable property of the light pulse is affected by the organic material; said method comprising the steps of:

(a) exciting said light-emitting diode means with a first drive current for a first period of time;

(b) exciting said light-emitting diode means with a second drive current for a second period of time immediately subsequent said first period of time;

(c) monitoring the light pulses received by said phototransistor means during said first and second periods of time to determine the change in said light pulses as a result of having come in contact with the organic material; and (d) processing the amount of change identified in step (c) to determine a desired property of the organic material.

33. The method of claim 32 wherein the second drive current level used in step (b) to excite said light-emitting diode means is less than the first drive current level used in step (a).

34. The method of claim 32 wherein said organic material being analyzed by said medical sensor comprises blood, and further wherein the detectable property monitored by said medical sensor is the amount of the light pulse that is reflected from said blood, said reflected light amount being relatable by the processing of step (d) to the amount of oxygen in the blood.

* * * * *

UNITED STATES PATENT AND TRADEMARK OFFICE
CERTIFICATE OF CORRECTION

PATENT NO. : 4,815,469

DATED : 03/28/89

INVENTOR(S) : Donald M. Cohen; James E. Barcel; and Michael D. Hooven

It is certified that error appears in the above-identified patent and that said Letters Patent is hereby corrected as shown below:

In the Drawings:

Sheet 8, Fig. 18, reverse the position of diode 204, so that the anode of diode 204 previously coupled to input terminal 132, is now coupled to tip electrode 170, and the cathode of diode 204 previously coupled to tip electrode 170, is now coupled to input terminal 132.

The above-identified correction has been made in Fig. 18 shown below:

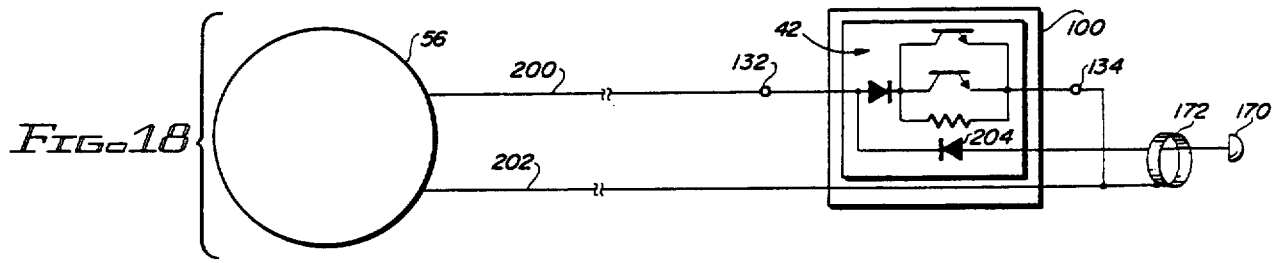

Signed and Sealed this

Twenty-second Day of November, 1994

Attest:

BRUCE LEHMAN

Attesting Officer

Commissioner of Patents and Trademarks